United States Patent [19]

Eisentraut et al.

[11] Patent Number: 5,506,677
[45] Date of Patent: Apr. 9, 1996

[54] ANALYSIS OF WEAR METALS IN PERFLUORINATED FLUIDS

[75] Inventors: Kent J. Eisentraut, Xenia; David W. Johnson, Fairborn, both of Ohio

[73] Assignee: The United States of America as represented by the Secretary of the Air Force, Washington, D.C.

[21] Appl. No.: 394,081

[22] Filed: Feb. 21, 1995

[51] Int. Cl.$^6$ .............................. G01N 21/71; G01J 1/02
[52] U.S. Cl. ........................................... 356/316; 356/243
[58] Field of Search ..................................... 356/311, 316, 356/243

[56] References Cited

U.S. PATENT DOCUMENTS 5,383,019  1/1995  Farrell et al. ........................... 356/316

OTHER PUBLICATIONS

C. S. Springer, Jr., D. W. Meek, and R. E. Sievers, "Rare Earch Chelates of 1,1,1,2,2,3,3,–Heptafluoro–7,7–dimethyl–4,6–octanedione", Inorganic Chemistry, vol. 6, No. 6, Jun. 1967, pp. 1105–1110.

Primary Examiner—F. L. Evans
Attorney, Agent, or Firm—Charles E. Bricker; Thomas L. Kundert

[57] ABSTRACT

Soluble metal complexes for use as standards in wear metal analysis of PFPAE fluids are provided. These standards are the metal complexes of 2,2-dimethyl-6,6,7,7,8,8,8,-heptafluoro-3,5-octanedione (HFOD). These complexes are soluble in PFPAE's to at least 100 ppm metal and are stable over a long period of time (months) in the presence of air. Generally, the metals of interest are Al, Na, Mg, Ca, Ba, Ni, Cu, Zn, Cd, Pb, Hg, Fe, Cr, Mn, V, Mo, Si, Ag, Na, Sn, Ti and Co. Also provided is a method for determining the concentration of at least one wear metal in a PFPAE fluid. This method is particularly suitable for determining determining the concentration of at least one wear metal in a PFPAE fluid by inductively coupled plasma-atomic emission spectroscopy.

5 Claims, No Drawings

ANALYSIS OF WEAR METALS IN PERFLUORINATED FLUIDS

RIGHTS OF THE GOVERNMENT

The invention described herein may be manufactured and used by or for the Government of the United States for all governmental purposes without the payment of any royalty.

BACKGROUND OF THE INVENTION

This invention is related to the determination of trace metals dissolved in perfluorinated fluids.

Perfluoropolyalkylethers (PFPAE) are being developed by the U.S. Air Force as high temperature lubricants for the next generation of turbine engines. These fluids consist essentially of a mixture of fluorinated polyethers. For example, these fluids can be of the general formula $R_fO(Z)_m(Y)_nR_f$, wherein $R_f$ is a lower perfluoroalkyl group, such as $CF_3$, $C_2F_5$, $C_3F_7$ and the like, wherein Z is $-CX_2CX_2O-.-CX_2CX_2CX_2O-$ or $-CX_2OCX_2CX_2O-$, wherein X is $-F$, $-CF_3$, $-C_2F_5$ and the like, and Y is $-CFXO-$, m and n are integers whose sum is between 2 and 200 and the ratio of n to ra is 0.1 to 10, and the Z and Y units are statistically distributed along the PFPAE chain. Commercial base fluids of this type have been available for some time, for example, Krytox® (DuPont), Fomblin® (Ausimont), Demnum® (Daikin) and the like.

While several PFPAE based lubricants are commercially available, there are no analytical methods for the analysis of metals, due to wear of bearing surfaces in these fluids. Analytical methods which are commonly used for conventional lubricants fall due to the insolubility of available metal standards in PFPAE fluids. Such methods include atomic absorption spectroscopy, emission spectroscopy, inductively coupled plasma-atomic emission spectroscopy (ICP-AES) and the like.

ICP-AES analysis is a technique for determining major, minor and trace elemental constituents of liquid samples. This technique is based upon generation of an inductively coupled plasma utilizing RF energy. Liquid samples are converted into an aerosol utilizing a nebulizer and injected into a plasma. As a sample enters the plasma, it undergoes desolvation, volatilization, atomization, excitation and finally emits photons characteristic of wavelengths of elements present in the sample. The intensity of the emission at characteristic wavelengths is used to determine the concentration of a element present in the sample while the wavelengths themselves determine what elements are present. The plasma is typically supported by argon gas, but other gases may also be employed. The most commonly used frequency for maintaining the plasma has been 27.12 Mhz, however, recently other frequencies including 40.68 Mhz have been employed.

Accordingly, it is an object of the present invention to provide metal standards for spectroscopic analysis which are both soluble and stable in PFPAE lubricants.

It is another object of the present invention to provide a method for the spectroscopic determination of wear metals in PFPAE lubricants.

Other objects and advantages of the present invention will be apparent to those skilled in the art.

DESCRIPTION OF THE INVENTION

In accordance with the present invention there are provided soluble metal complexes for use as standards in wear metal analysis of PFPAE fluids. These standards are the metal complexes of 2,2-dimethyl-6,6,7,7,8,8,8-heptafluoro-3,5-octanedione (HFOD). These complexes are soluble in PFPAE's to at least 100 ppm metal and are stable over a long period of time (months) in the presence of air. Generally, the metals of interest are Al, Na, Mg, Ca, Ba, Ni, Cu, Zn, Cd, Pb, Hg, Fe, Cr, Mn, V, Mo, Si, Ag, Na, Sn, Ti and Co.

Also provided is a method for determining the concentration of at least one wear metal in a PFPAE fluid which comprises the steps of:

(a) operating the spectroscopy apparatus so as to generate a spectrum with at least one known concentration of at least one metal standard, wherein said metal standard consists essentially of a metal complex of 2,2-dimethyl-6,6,7,7,8,8,8-heptafluoro-3,5-octanedione;

(b) scanning the obtained spectrum to obtain a first set of spectral data comprising spectral intensity and spectral position for each metal in said standard;

(c) operating the spectroscopy apparatus so as to generate a spectrum with an unknown sample which contains at least one looked-for element in the unknown sample to be determined;

(d) scanning the obtained spectrum to obtain a second set of spectral data comprising spectral intensity and spectral position for each metal in said unknown sample; and (e) determining the presence and quantity of wear metals by comparing the spectral intensity/position of said second set of spectral data with the spectral intensity/position of said first set of spectral data.

This method is particularly suitable for determining determining the concentration of at least one wear metal in a PFPAE fluid by inductively coupled plasma-atomic emission spectroscopy.

In general, the standards are prepared by reacting a metal salt with HFOD in a suitable solvent, precipitating the resulting complex in water and recovering the complex. Generally, the metal salt can be a halide, nitrate, sulfate, acetate, or the like. Suitable solvents include absolute methanol, carbon tetrachloride, ethanol, methylcyclohexane and the like. Preparations are given in greater detail in the Examples which follow. The resulting standard complexes are insoluble in water, but often precipitate as hydrates. The presence of water of hydration can be shown by thermogravimetric analysis. In general, any water of hydration can be removed by heating the complex at 60° C. under vacuum for about 1 to 24 hours. Preparation of the aluminum complex differs in that the complex is not precipitated in water. The resulting complexes can be purified by vacuum sublimation or by recrystallization.

The analytical standards are prepared by dissolving appropriate quantities of the metal HFOD complex in either the perfluorinated fluid to be studied and/or a co-solvent such as Freon E6.5. A calibration curve is then established for each of the metals, using concentrations of the metal HFOD complex ranging from 1 ppm to 100 ppm, or greater. Once unique calibration curves have been established, it may be desirable to establish one or more calibration curves for several of the metals in combination. Several metal complexes can be dissolved in the fluid, Freon E6.5 or a mixture thereof, to provide a multielement metal standard. If Freon E6.5 is used, all standards and samples are prepared by mixing Freon and perfluorinated fluid in a 4:1 ratio by mass. The samples are then analyzed by atomic spectroscopy.

The present invention thus provides for the quantitative determination of metals in fluorinated fluids. Alternatively, the metal standards of this invention may be used for the analysis of metals in other difficult matrixes, including the fluorinated surfactants which are under consideration as synthetic blood substitutes.

The following examples illustrate the invention:

Example I

Preparation of analytical standards

Tris(2,2-dimethyl1-6,6,7,7,8,8,8-heptafluoro-3,5-octanedionato)aluminum $Al(FOD)_3$): 8.85 g (30 mmol) of HFOD dissolved in 50 ml $CCl_4$ was added to a slurry of 1.34 g (9.95 mmol) of $AlCl_3$ in 75 ml of $CCl_4$. The mixture was refluxed until HCl gas no longer evolved. After cooling to room temperature, the volume of the solution was reduced to 25 ml under vacuum. The solution was refrigerated overnight. The resulting crystalline solid was filtered and recrystallized from methylene chloride.

Tris(2,2-dimethyl-6,6,7,7,8,8,8-heptafluoro-3,5-octanedionato) complexes of Na, Mg, Ca, Ba, Ni(II), Cu(II), Zn, Cd, Pb(II) and Hg(II): These complexes were prepared by adding 5.92 g (20.0 mmol) of HFOD dissolved in 15 ml of methanol to a solution of the appropriate metal nitrate or chloride (10.0 mmol) dissolved in 25 ml of methanol. 5.05 ml of 3.97M aqueous sodium hydroxide was slowly added to the alcoholic solution. During the addition a precipitate formed, but on further addition, redissolved. The resulting solution was poured into 500 ml of aleionized water. In each case the resulting precipitate was filtered and recrystallized from methylene chloride. The crystalline solids were dried at 60° C. under vacuum for 1 hour and stored in a desiccator. Tris(2,2-dimethyl-6,6,7,7,8,8,8-heptafluoro-3,5-octanedionato) complexes of Fe(III), Cr(III), Mn(III), V(III) and Co(III): These complexes were prepared in a manner similar to that above.

Yield data and metal analyses are shown in table I, below:

TABLE I

| Complex | % Yield | % metal actual (calc) | % water actual (calc) | % residue | $T_{1/2}$ |
|---|---|---|---|---|---|
| Na(FOD) | 56 | 7.12 (7.23) | | | |
| Mg(FOD)$_2$ | 80 | 3.91 (3.96) | | 2.16 | 170 |
| Ca(FOD)$_2$ | 74 | 6.08 (6.18) | 2.76 (2.78) | 0.9 | 220 |
| Ni(FOD)$_2$ | 32 | 8.76 (8.80) | 2.97 (2.70) | 1.3 | 185 |
| Cu(FOD)$_2$ | 38 | 9.68 (9.72) | | 0.7 | 160 |
| Zn(FOD)$_2$ | 82 | 9.88 (9.97) | | 0.8 | 205 |
| Ba(FOD)$_2$ | 76 | 18.36 (18.42) | 2.44 (2.42) | 0.1 | 230 |
| Cd(FOD)$_2$ | 69 | 15.48 (15.60) | 3.90 (2.50) | 1.6 | 215 |
| Hg(FOD)$_2$ | 37 | 25.08 (25.37) | (2.28) | | |
| Pb(FOD)$_2$ | 39 | 26.02 (25.98) | | 0.9 | 185 |
| Al(FOD)$_3$ | 65 | 2.94 (2.96) | | 0.1 | 160 |
| V(FOD)$_3$ | 40 | 5.38 (5.44) | | 1.7 | 195 |
| Cr(FOD)$_3$ | 43 | 5.51 (5.55) | | 1.0 | 155 |
| Fe(FOD)$_3$ | 51 | 5.95 (5.93) | | 0.9 | 165 |
| Mn(FOD)$_3$ | 47 | 5.77 (5.84) | | | |
| Co(FOD)$_3$ | 45 | 6.19 (6.24) | | 0.8 | 175 |

The complexes were all found to be soluble in Krytox 143AC, Fomblin Z and Freon E6 to at least 100 ppm. Solutions of each metal HFOD complex were examined using ICP to determine if the wavelengths available on the polychrometer would suffer from any serious interferences. Only the aluminum complex showed any interference. The observed interference is similar to the interference observed when aluminum is analyzed in hydrocarbon oils.

Example II

The standards for aluminum, iron, chromium, cobalt, nickel, and zinc were selected for more thorough study. A calibration curve for each of these metals, using concentrations from 1 ppm to 100 ppm was measured with the results shown in Table II, below. Also contained in Table II is the estimate of the detection limit based on three times the standard deviation of the readings of the blank solution. Detection limits for the various metals in solution are in the range of 1-50 ppb under the conditions of this analysis, corresponding to concentrations between 5 and 250 ppb in the original oil sample.

TABLE II

| Element | 1 | Correlation Coefficient | Detection Limit (ppb) | Oil Detection Limit (ppb) |
|---|---|---|---|---|
| Al | 308.2 | 0.999 | 44 | 220 |
| Ba | 493.4 | 1.000 | 1 | 5 |
| Cd | 228.8 | 1.000 | 8 | 38 |
| Co | 228.6 | 0.994 | 18 | 90 |
| Cr | 267.7 | 0.999 | 32 | 160 |
| Cu | 324.7 | 1.000 | 14 | 71 |
| Fe | 259.9 | 1.000 | 8 | 40 |
| Mg | 279.5 | 0.999 | 2 | 10 |
| Na | 588.9 | 0.999 | 20 | 100 |
| Ni | 231.6 | 0.999 | 24 | 120 |
| Zn | 213.8 | 0.999 | 28 | 140 |

Example III

Table III, below, shows the results of an experiment where weighed amounts of six of the complexes were mixed. The instrument was standardized using the individual solutions of the six metal ions and then the mixed solution was analyzed. The metal analysis of the resulting solution shows deviations between 0.5 and 1.5%. The same solution was analyzed after one week had passed, giving essentially the same results.

TABLE III

Analysis of a Mixed Metal Standard

| Metal | Actual ppm | 0 Days Found ppm (% RSD) | % Dev | 7 Days Found ppm (% RSD) | % Dev |
|---|---|---|---|---|---|
| Al | 16.8 | 16.6 (0.5) | −1.2 | 16.4 (1.0) | −2.4 |
| Co | 16.6 | 16.5 (0.6) | −0.6 | 16.7 (0.8) | +0.6 |
| Cr | 17.7 | 17.6 (0.2) | −0.6 | 17.5 (1.1) | −1.2 |
| Fe | 17.5 | 17.3 (0.2) | −1.1 | 17.3 (0.9) | −1.1 |
| Ni | 16.4 | 16.1 (0.4) | −1.8 | 16.2 (1.0) | −1.2 |
| Zn | 21.7 | 21.5 (0.4) | −0.9 | 21.4 (0.8) | −1.4 |

These results indicate that several metal complexes can be combined into a single standard solution. The standard deviation of the immediate (0 days) determinations is relatively small. The standard deviation of the analysis of the week old solution is somewhat large, in part due to only a small number (3) of determinations being made. Various modifications may be made in the instant invention without departing from the spirit and scope of the appended claims.

We claim:

1. A method for determining the concentration of at least one wear metal in a PFPAE fluid which comprises the steps of:

(a) operating a spectroscopy apparatus so as to generate a spectrum with at least one known concentration of at least one metal standard, wherein said metal standard consists essentially of a metal complex of 2,2-dimethyl-6,6,7,7,8,8,8-heptafluoro-3,5-octanedione;

(b) scanning the obtained spectrum to obtain a first set of spectral data comprising spectral intensity and spectral position for each metal in said standard;

(c) operating said spectroscopy apparatus so as to generate a spectrum with an unknown sample which contains at least one looked-for element in the unknown sample to be determined;

(d) scanning the obtained spectrum to obtain a second set of spectral data comprising spectral intensity and spectral position for each metal in said unknown sample; and (e) determining the presence and quantity of wear metals by comparing the spectral intensity/position of said second set of spectral data with the spectral intensity/position of said first set of spectral data.

2. The method of claim 1 wherein said metal in said standard is selected from the group consisting of Al, Na, Mg, Ca, Ba, Ni, Cu, Zn, Cd, Pb, Hg, Fe, Cr, Mn, V, Mo, Si, Ag, Na, Sn, Ti and Co.

3. The method of claim 1 wherein said spectroscopy apparatus is an inductively coupled plasma-atomic emission spectroscope.

4. A standard for the wear metal analysis of a PFPAE fluid consisting essentially of a known quantity of a metal complex of 2,2-dimethyl-6,6,7,7,8,8,8-heptafluoro-3,5-octanedione in said fluid.

5. The standard of claim 4 wherein the metal in said metal complex is selected from the group consisting of Al, Na, Mg, Ca, Ba, Ni, Cu, Zn, Cd, Pb, Hg, Fe, Cr, Mn, V, Mo, Si, Ag, Na, Sn, Ti and Co.

* * * * *

UNITED STATES PATENT AND TRADEMARK OFFICE
CERTIFICATE OF CORRECTION

PATENT NO. : 5,506,677

DATED : April 9, 1996

INVENTOR(S) : Kent J. Eisentraut et al

It is certified that error appears in the above-indentified patent and that said Letters Patent is hereby corrected as shown below:

Col. 1, line 23 "ra" should read ---m---.

Col. 1, line 33, "fall" should read ---fail---.

Col. 3, line 27, "aleionized" should read ---deionized---.

Signed and Sealed this

First Day of October, 1996

Attest:

BRUCE LEHMAN

Attesting Officer    Commissioner of Patents and Trademarks